United States Patent
Ng

(10) Patent No.: US 6,458,361 B1
(45) Date of Patent: Oct. 1, 2002

(54) METHOD OF PRODUCING A LIQUID COMPOSITION COMPRISING GINSENG, CORDYCEPS, AND GANODERMA LUCIDUM

(76) Inventor: Michael S. Ng, 8383 Wilshire Blvd., Suite 360, Beverly Hills, CA (US) 90211

( * ) Notice: Subject to any disclaimer, the term of this patent is extended or adjusted under 35 U.S.C. 154(b) by 0 days.

(21) Appl. No.: 09/906,450

(22) Filed: Jul. 17, 2001

(51) Int. Cl.[7] ......................... A61K 35/84; A61K 35/78
(52) U.S. Cl. .................. 424/195.15; 424/725; 424/728; 424/757
(58) Field of Search ............ 424/195.15, 728, 424/725, 757

(56) References Cited

U.S. PATENT DOCUMENTS 5,744,187 A * 4/1998 Gaynor

FOREIGN PATENT DOCUMENTS

| CN | 1223135 | * | 7/1999 |
| CN | 1245692 | * | 3/2000 |
| CN | 1286051 | * | 3/2001 |

OTHER PUBLICATIONS

"Tien Hsien Liquid" described in UMDG.com wesite of United Medical Development Group. 2000. 1 page.*
Chen et al. J. Trad. Chinese Med. 1993. vol. 13, No. 3, pp. 223–226, Medline Abstract enclosed.*

* cited by examiner

Primary Examiner—Christopher R. Tate
(74) Attorney, Agent, or Firm—Raymond Y. Chan; David and Raymond Patent Group

(57) ABSTRACT

A producing method of Tien Hsien Liquid which mainly comprises ginseng, cordyceps, and ganoderma lucidum, including the steps of: soaking and heating the ginseng, cordyceps, ganoderma lucidum in water with honey and sorbic acid dissolved therein to form an extract solution; mixing and stirring the extracted solution with supplemental solution to form a combined solution; adding a predetermined amount of powder pearl into the combined solution; and filtering out the combined solution to obtain the Tien Hsien Liquid.

61 Claims, 3 Drawing Sheets

METHOD OF PRODUCING A LIQUID COMPOSITION COMPRISING GINSENG, CORDYCEPS, AND GANODERMA LUCIDUM

BACKGROUND OF THE PRESENT INVENTION

1. Field of Invention

The present invention relates to herbal health product, and more particularly to a producing method of Tien Hsien Liquid.

2. Description of Related Arts

According to Chinese (herbal) medicine, Ginseng is reputed to be effective in shock, collapse of the cardiovascular system, hemorrhaging, and heart failure. Clinical trails on volunteers show that ginseng extract can substantially slow down the heart rate and reduce oxygen demand. Besides, in Chinese medical journals, there have been reported on the effectiveness of a ginseng decoction in combination with other herbs in the treatment of cardiogenic shock and acute myocarditis. Therefore, if we successfully find out and extract that functional chemical from the ginseng and other herbs, the patients can effectively take dose of concentrated functional chemical as the herbal medicine instead of having the whole plant of ginseng. Like the Western medicine, it is more efficient and effective.

SUMMARY OF THE PRESENT INVENTION

The main object of the present invention is to provide a producing method of Tien Hsien Liquid, wherein the Tien Hsien liquid mainly is extracted mainly from ginseng, cordyceps, ganoderma lucidum, and honey. The therapeutical function of ginseng is mainly for tonic, stimulant, regulating sugar and cholesterol levels, and stimulating the immune system. The cordyceps exhibits an immunopotentiating effect in treating cancer and immunodeficient patients. The ganoderma lucidum contains ergosterol, fungal lysozyme, proteinase, several amino acids, and organic acids. These functional elements are extracted in form of liquid to form a composition named as Tien Hsien liquid for achieving a combined herbal health product.

Accordingly, in order to accomplish the above object, the present invention provides a Tien Hsien Liquid produced according to a producing method comprising the steps of:

(a) soaking a plurality of ingredients, which includes 11–20% by weight of ginseng, 30–50% by weight of cordyceps, 11–20% by weight of ganoderma lucidum, and 10% or less by weight of honey, in a predetermined weight of water within an extracting container to form a soaking solution, wherein the weight of water is equal to a total weight of the ingredients;

(b) heating the soaking solution to a temperature higher than a boiling point of the soaking solution in a closed chamber of the extracting container while mixing and stirring the soaking solution for a predetermined period of time to form a combined solution with residuals of the ginseng, cordyceps and ganoderma lucidum; and (c) removing the residuals of the ginseng, cordyceps and ganoderma lucidum to form the soaking solution to form an extracted solution to form the Tien Hsien liquid.

DETAILED DESCRIPTION OF THE PREFERRED EMBODIMENT

Figure 1:
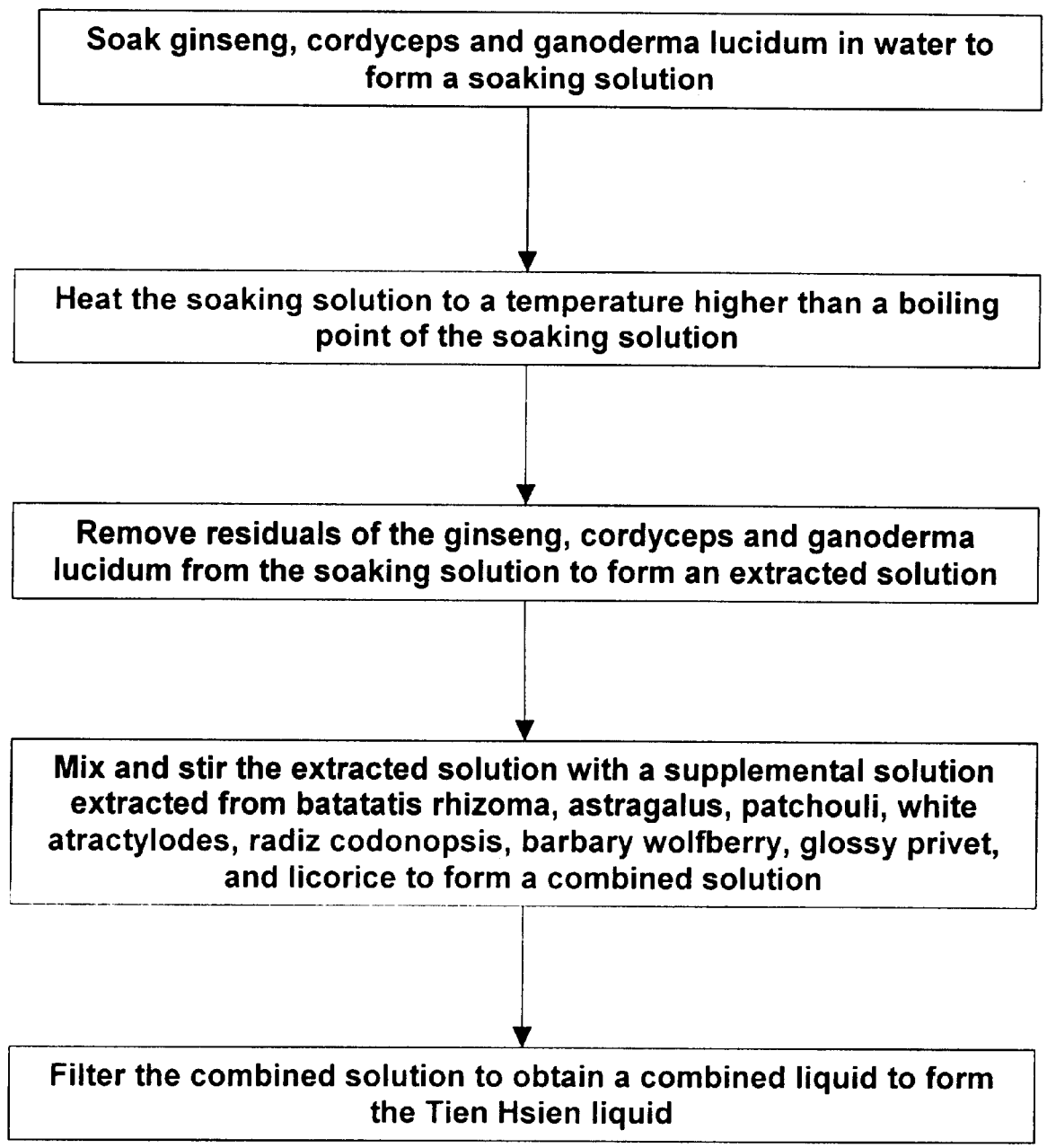
FIG. 1 is a flow chart of a producing method of Tien Hsien Liquid according to a preferred embodiment of the present invention.
Figure 2:
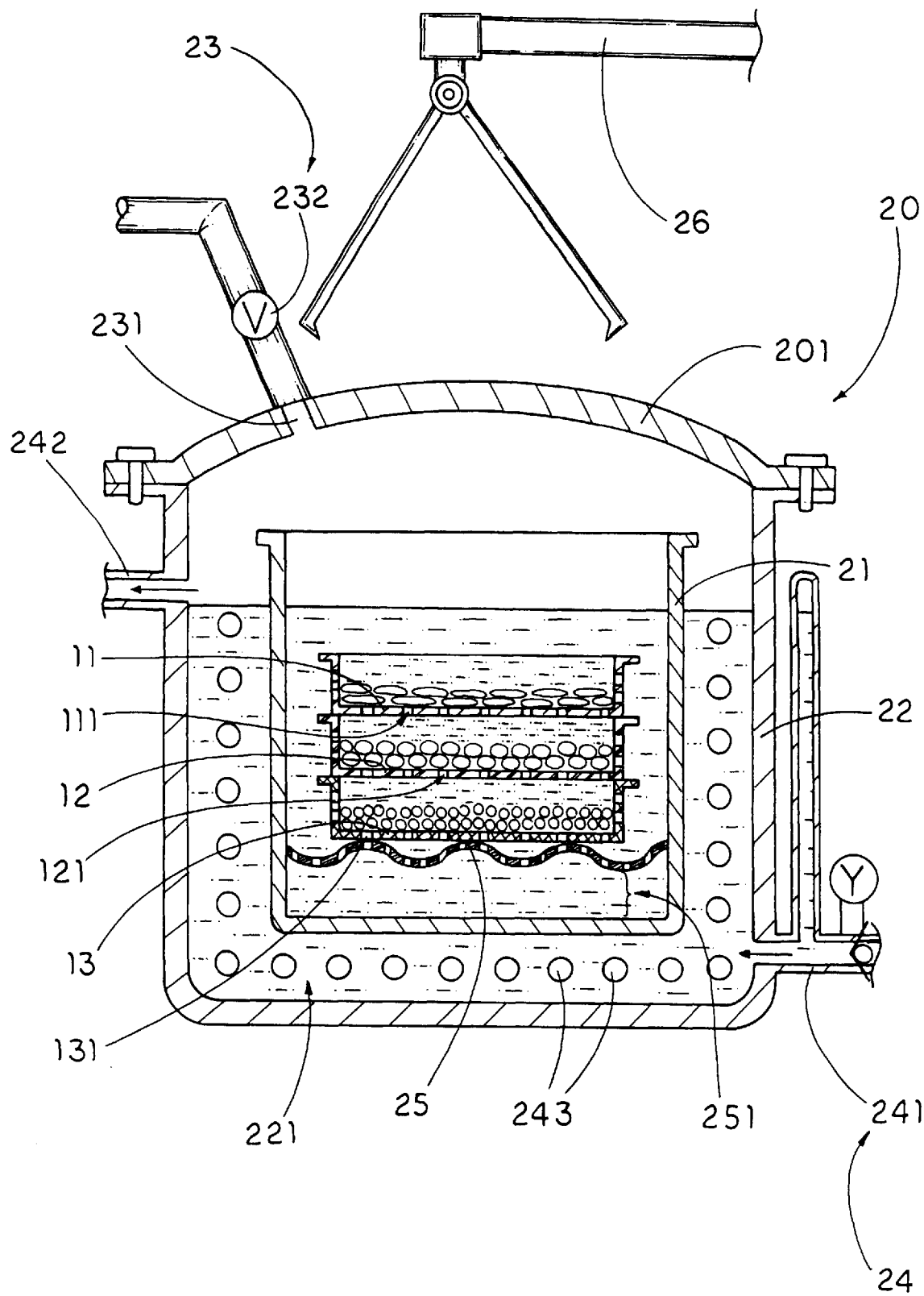
FIG. 2 is a sectional view illustrating a first phase of the producing method according to the above preferred embodiment of the present invention, showing an extracting container.
Figure 3:
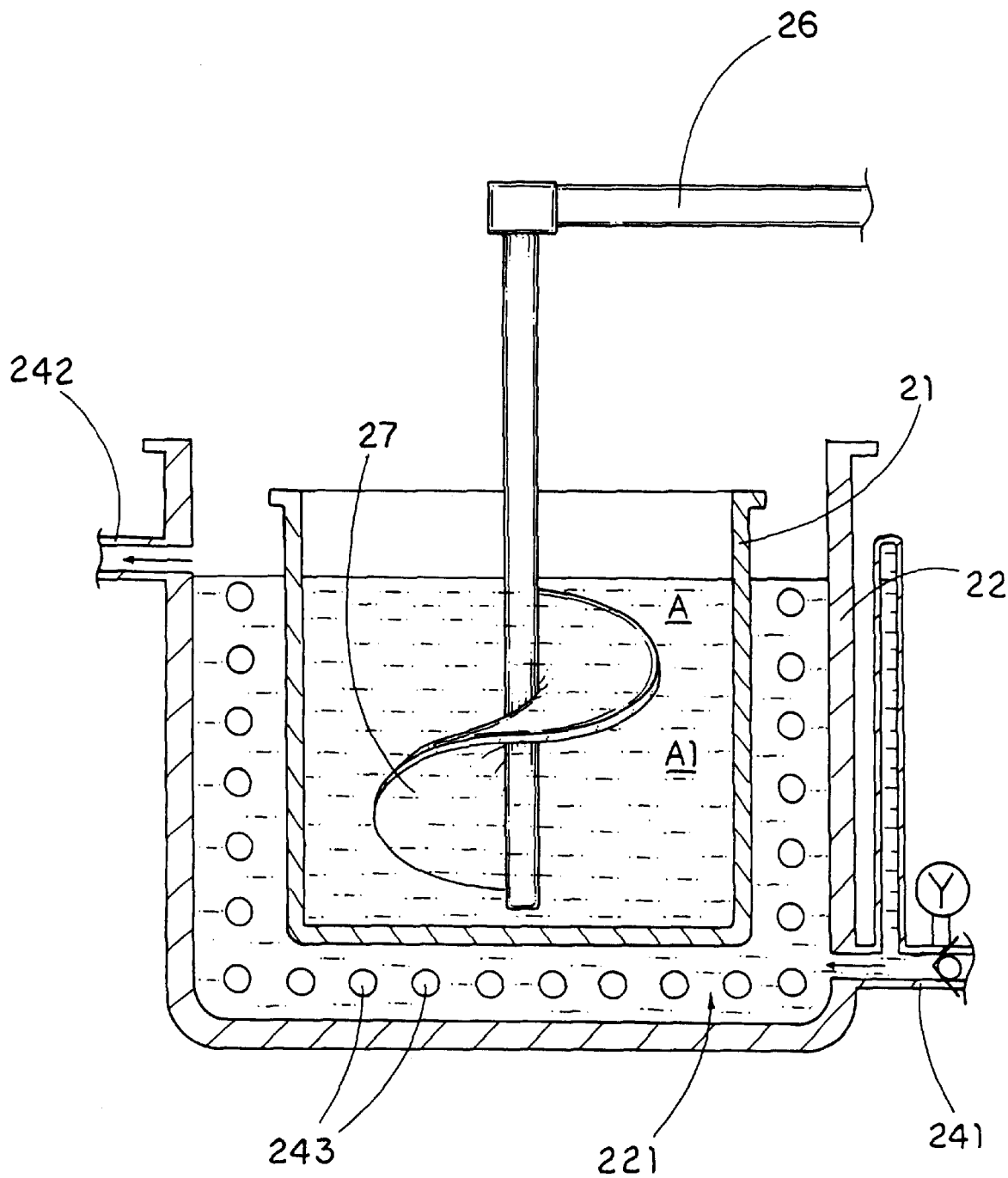
FIG. 3 is a sectional view illustrating a second phase of the producing method according to the above preferred embodiment of the present invention, showing the extracting container incorporating with a stirring apparent.

Referring to FIGS. 1 to 3, a Tien Hsien liquid produced according to a producing method is illustrated, wherein the process method generally comprises the steps of:

(a) soaking a plurality of ingredients, which includes 11–20% by weight of ginseng, 30–50% by weight of cordyceps, and 11–20% by weight of ganoderma lucidum, in a predetermined weight of water within an extracting container 20 to form a soaking solution, wherein the weight of water is equal to a total weight of the ingredients;

(b) heating the soaking solution to a temperature higher than a boiling point of the soaking solution in a closed chamber of the extracting container 20 while mixing and stirring the soaking solution every predetermined time interval; and (c) removing the residuals of the ginseng, cordyceps and ganoderma lucidum from the soaking solution to form an extracted solution and filtering extracted precipitates of the extracted solution to obtain an extracted liquid.

In the step (a), according to a preferred embodiment of the present invention, the ingredients include 425 mg of ginseng, 1150 mg of cordyceps and 425 mg of ganoderma lucidum are soaked in 2000 mg of water with honey and sorbic acid to form the soaking solution.

According to the Chinese pharmacopoeia, "Compendium of Material Medica", the traditional uses of ginseng are replenishes and supplements original ch'I, expels evil ch'i; supplements lung yin (vital essence), benefits the body fluid of the five viscera (heart, liver, spleen, lungs, and kidneys); pacifies the soirit, soothes the soul, increases wisdom, and opens the cleverness of the heart; and controls palpitations, increases salivation, and clears vision.

For thousands of years, ginseng has been used by the common people as a tonic and in emergency medicine to rescue dying patients, and by the rich as a rejuvenating and revitalizing agent.

The chemical constituents of the ginseng are the following:

(1) Essential oils (0.05%): panaxynol, $\beta$-elemene, panacene, and panaxin.

(2) Saponins (4%): ginsenisides —Ro, —Ra, —$Rb_1$, —$Rb_2$, —Rc, —Rd, —Re, —Rf, $Rg_{13}$, —Rg, —Rh, (the sapogenin of ginsenoside —Ro being oleanolic acid, of gensenosides —$Rb_1$, —$Rb_2$, —Rc, —Rd being 20-S-protopanaxadiol, of gensenosides —Re, Rf, $Rg_1$, $Rg_2$ being 20-S-protopanaxatriol).

(3) Sugars: monosaccharides about 1.5% (D-glucose, D-fructose), disaccharides (sucrose, maltose), triaccharides (trisaccharides A, B, C); (4) $\beta$-sitosterol, $\beta$-sitosteryl-glucoside, vitamin B, choline. It is worth to mention that ginsenosides are found to be effective in the treatment of cancer patients.

The gensenoside has a chemical formula as follows:

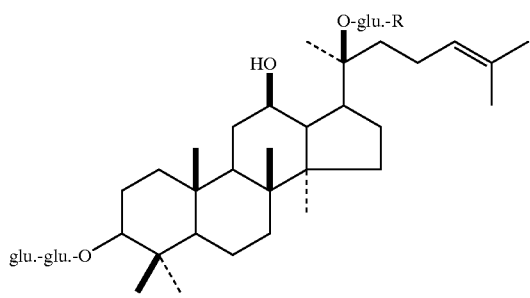

ginsenoside Rb$_1$   R = glu.
ginsenoside Rc    R = ara.(f)

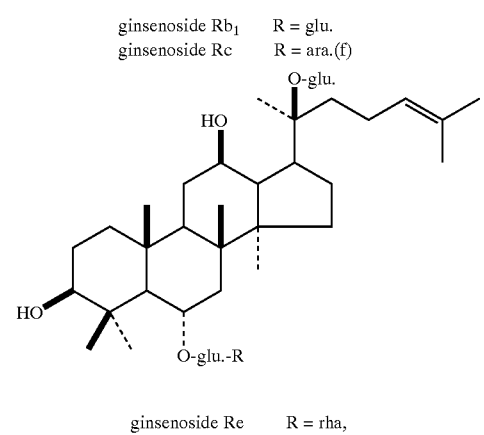

ginsenoside Re    R = rha,
ginsenoside Rg$_1$    R = H

Many herbs have long been known to affect the immune system, but only recent have scientists considered them and adjunct cancer therapies. Such herbs, one of which is ginseng, often prompt the body's cell to secrete cytokines, which then enhance the immune response. Besides, the pharmacology of the ginseng is the following:

(1) Tonifying effect: Ginseng acts on the pituitary and stimulates the adrenal gland, thus increasing the body's resistance to harmful stimulation or stress, and allowing the body to withstand extreme temperatures.

(2) Nervous system-stimulating effect: Ginseng hastens nervous reflexes, speeds up transmission of nervous impulses, increases the intensity of conditioned reflexes, improves the ability to think analytically and overall mental performance, and diminishes fatigue. The crude saponin of ginseng stimulates the central nervous system and acts against muscular fatigue and tension.

(3) Cardiotonic effect: Ginseng causes the heart to contract more strongly, as do the cardio-glycosides. The alcohol extract is more potent in this action than the aqueous extract. Animal studies show that small doses of ginseng cause contraction of peripheral blood vessels, thus slightly increasing blood pressure.

(4) Stimulating sexual functions: Ginseng stimulates the hormones of sex glands, thus increasing sexual function in males and females.

(5) Hypoglycemic effect: Ginseng affects metabolism and lowers blood sugar level by acting synergetically with insulin.

(6) Antidiuretic effect: Ginseng's antidiuratic action is similar to that of desoxycorticosterone in increasing secretion of aldosterone, causing retention of sodium, thus decreasing excretion of urine.

(7) Effect on digestion, absorption, and metabolism: Ginseng increases protein synthesis and also appetite, and causes a lowering of blood cholesterol.

(8) Antiallergic effect: Ginseng decreases allergic shock caused by horse blood serum, and dramatically inhibits edema due to allergy. These actions are probably due to ginseng's antihistamine actions.

(9) Other effects:
   (a) Ginsenoside R$_1$ possesses a slight sedative action.
   (b) Ginsenoside Rb$_2$, Re, Rg$_1$ stimulates DNA, protein, and fat synthesis in mice bone-marrow cells.
   (c) Ginsenoside—Rg$_1$ diminishes fatigue.
   (d) Ginsenoside—Rb$_1$ prevents blood hemolysis.
   (e) Ginseng promotes the process of hemopoiesis.

The chemical constituents of the cordyceps are cordycepic acid and cordycepin, which have the chemical formulas as follow:

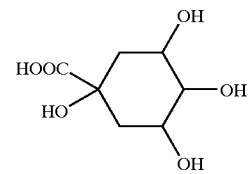

cordycepic acid

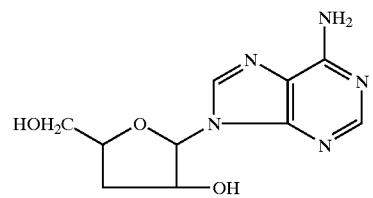

cordycepin

The pharmacology of the cordyceps is the following:

(1) Bronchial effect: It dramatically dilates extirpated animal bronchi.

(2) Sedative effect: It sedates and induces sleeping in mice.

(3) Antibacterial effect: In vitro cordycepic acid inhibits staphylococci, streptococci and other types of bacteria.

(4) Other effects: Intravenous injection of the extract causes the blood pressure to drop and inhibits the activity of intestinal tract, uterus, and heart.

The Ganodema lucidum contains ergosterol, fungal lyozyme, proteinase, several amino acids, and organic acids. Recently, several polysaccharides have been isolated from Ganoderma lucidum Konst. Further, in addition to the alkaloid, ganodespurine, other compounds including ganodeiol A, genoderiol B, ganodermatriol, and ganolactone I have been isolated from this fungus.

The ergosterol, ganodespurine, and genosporelactone A and B have the chemical formulas as follow:

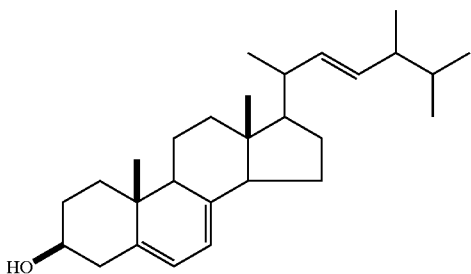

Ergosterol

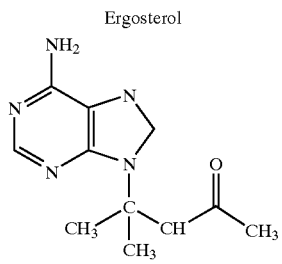

Ganodespurine

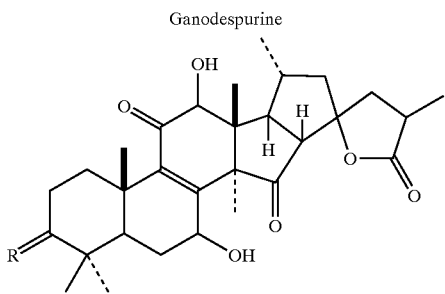

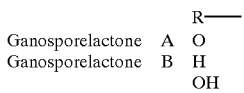

|  | R— |
|---|---|
| Ganosporelactone A | O |
| Ganosporelactone B | H OH |

The extracting container 20 comprises an inner casing 21 for receiving a first basket 11, a second basket 12 and a third basket 13 therein, an outer casing 22 for receiving the inner casing 21 therein so as to define a water cavity 221 between the inner casing 21 and the outer casing 22 to receive a heat medium such as water, and a cover 201 adapted for sealedly covering up the outer casing 22 for maintaining a predetermined pressure and temperature of the extracting container 20.

The step (a) comprises the following steps:
(a-1) Cut the ginseng, cordyceps and ganoderma lucidum in pieces each having a size less than 5 cm.
(a-2) Put the ginseng, cordyceps and ganoderma lucidum in the first, second and third baskets 11, 12, 13 respectively, wherein the first, second, and third baskets 11, 12, 13, as shown in FIG. 2, are identical racks each having a plurality of mesh holes 111, 121, 131 provided on all surfaces. The second basket 12 is piled on top of the third basket 13 while the first basket 11 is piled on top of the second basket 12. The mesh holes of the first, second and third baskets 11, 12, 13 must be smaller than the sizes of the ginseng, cordyceps and ganoderma lucidum respectively so that the boiling water is capable of passing through the mesh holes 111, 121, 131.
(a-3) Completely soak the ginseng, cordyceps and ganoderma lucidum in water by fully immersing the first, second and third baskets 11, 12, 13 into an inner casing 21 of the extracting container 20.

As shown in FIG. 2, the first, second, and third baskets 11, 12, 13 are piled up in the inner casing 21 of the extracting container 20 orderly by putting the first basket 11 on top, the third basket 13 at the bottom, and the second basket 12 between the first and third baskets 11, 13, wherein heat is evenly applied to the extracting container 20 to maintain the boiling soaking solution inside the inner casing 21 at a predetermined temperature.

The extracting container 20 further comprises a pressure control 23 for controlling the pressure inside the extracting container 20 and a water temperature control 24 for controlling the temperature of the extracting container 20.

The pressure control 23 comprises a gas release valve 231 provided on top thereof for releasing interior gas such as steam, especially before opening the cover 201, and a pressure gauge 232 for measuring the interior pressure of the extracting container 20, so as to maintain the predetermined pressure inside the extracting container 20. In other words, the ingredients are soaked in the extracting container 20 under a predetermined pressure within a predetermined period of soaking time.

The water temperature control 24 comprises a water inlet 241, a water outlet 242 for communicating with the water cavity 221 so as to enable water flowing into the water cavity 221 from the water inlet 241 and flowing out through the water outlet 242, an electric heating device 243 operatively disposed in the water cavity 221 for heating up the water therein so as to maintain an even temperature of the water within the water cavity 221, and a water level gauge 244 upwardly extended from the water inlet 241 for indicating the water level of the water inside the water cavity 221. It is worth to mention that, since water will be evaporated when heat is applied thereto, water will be gradually fed into the water cavity 221 to compensate the water loss in the water cavity so as to maintain a predetermined water level that fully covers the electric heating device 243 in the water cavity 221.

Therefore, in the step (b), the electric heating device 243 heats up the water in the water cavity 221 to form a water bath so as to indirectly heat up the ginseng, cordyceps and ganoderma lucidum inside the inner casing 21 to form the soaking solution. Since the soaking solution is a concentrated solution, the water bath can provide an even, continuous and gentle heat to the inner casing 21 so as to prevent the soaking solution from being burnt.

The extracting container 20 further comprises a base divider 25 transversely provided on a bottom portion of the inner casing 21 of the extracting container 20 for supporting the first, second, and third baskets 11, 12, 13 in such a manner that a gap 251 is defined between the base divider 25 and a bottom surface of the inner casing 21 for enhancing the circulating of the soaking solution inside the inner casing 21, as shown in FIG. 2.

In the step (a), the ingredients are immersed into the water inside the inner casing 21 of the extracting container 20 while the water is at room temperature.

The step (b) further comprises the steps of:
(b-1) heating the room temperature water inside the inner casing for about 30 to 45 minutes until the soaking solution is boiled; and
(b-2) inter-changing the piled-up positions of the first, second, and third baskets 11, 12, 13 are taken out of the extracting container 20 vertically so as to move the first basket 11 underneath the third basket 13.

Therefore, the second basket 12 is on a top position, the first basket 11 is at the bottom position, and the third basket 13 is positioned between the second and first basket 12, 11. In other words, one of the baskets 11, 12, 13 at the bottom position is switched to a top position every predetermined time interval.

Since it is impossible to continuously stir and mix the soaking solution during heating the ingredients in the baskets 11, 12, 13 placed inside the inner casing 21, the present invention finds a new way to mix and stir the soaking solution and ensures the water content in different levels inside the inner casing 21 has chance to contact with different ingredients. That is, according to the present invention, by changing the positions of the first, second and third baskets 11, 12, 13, the soaking solution at different levels, i.e. the upper level, mid-portion level and lower level, can contact with different ingredients every predetermined time interval so as to soak the ingredients at different positions. Moreover, the taking out and placing back actions of the baskets 11, 12, 13 can well mix and stir the soaking solution. The step (b-2) is repeated until the necessary chemicals from the ingredients are extracted into the soaking solution. According to the present invention, the step (b) takes about 4 hours to complete.

In order to take out and place back all the baskets 11, 12, 13 from the extracting container 20, a lift arm 26 is incorporated in such a manner that when the cover 201 is opened, the lift arm 26 is lowered to hold all the baskets 11, 12, 13 and lift up the baskets 11, 12, 13 from inner casing 21 of the extracting container 20 for inter-changing the positions of the baskets 11, 12, 13. Afterwards, the lift arm 26 can be used to place the baskets with inter-changed positions back inside the inner casing 21 of the extracting container 20.

In the step (c), the residuals of the ingredients are removed from the soaking solution to form the combined solution by taking out the baskets 11, 12, 13 from the inner casing 21 by means of the lift arm 26. The combined solution inside the inner casing is poured out to filter the extracted precipitates of the combined solution to form the extracted solution, wherein all the necessary chemicals from the ingredients are extracted into the extracted solution.

The producing method of the present invention further comprises the steps of:

(d) mixing and stirring the extracted liquid with a supplemental solution to form a combined solution; and (e) filtering the combined solution to obtain a combined liquid.

In the step (d), the ingredients of the supplemental solution include 8–22% by weight of Batatatis Rhizoma, 7–21% by weight of Astragalus, 4–12% by weight of Patchouli, 3–11% by weight of White Atractylodes, 3–11% by weight of Radiz Codonopsis, 3–11% by weight of Barbary Wolfberry, 2–6% by weight of Glossy Privet, and 2–6% by weight of Licorice. Preferably, ratios of all the ingredients of the combined liquid are 13% by weight of the ginseng, 36% by weight of the cordyceps, 13% by weight of the ganoderma lucidum, 9% by weight of the Batatatis Rhizoma, 8% by weight of the Astragalus, 5% by weight of the Patchouli, 4% by weight of the White Atractylodes, 4% by weight of the Radiz Codonopsis, 4% by weight of the Barbary Wolfberry, 2% by weight of the Glossy Privet, and 2% by weight of the Licorice.

The supplemental solution is produced by the following steps:

(1) Soak a plurality of supplemental ingredients, including 270 mg of Batatatis Rhizoma, 255 mg of Astragalus, 140 mg of Patchouli, 125 mg of White Atractylodes, 125 mg of Radiz Codonopsis, 125 mg of Barbary Wolfberry, 65 mg of Glossy Privet, and 65 mg of Licorice, in a predetermined weight of water within an extracting container 20, which can be the same extracting container 20 used in the step (a) or another individual extracting container, to form a supplemental soaking solution, wherein the weight of water is equal to a total weight of the supplemental ingredients;

(2) Heat the supplemental soaking solution to a temperature higher than a boiling point of the supplemental soaking solution in a closed chamber of the extracting container 20, i.e. the inner casing 21, while mixing and stirring the supplemental soaking solution every predetermined time interval.

(3) Remove the residuals of the supplemental ingredients from the supplemental soaking solution to form a supplemental extracted solution and filtering extracted precipitates of the supplemental extracted solution to obtain the supplemental solution.

In the step (d), as shown in FIG. 3, the supplemental solution and the extracted liquid are mixed together in the inner casing 21 of the extracting container 20 as used in the above step (a) and (b). Of course, another independent inner casing 21' can be used to receive the extracted liquid and the supplemental solution and then placed inside the outer casing 22 of the extracting container 20. Similarly, heat is applied to the inner casing 21' by the electric heating device 243 of the extracting container 20 to maintain a predetermined temperature inside the inner casing 21' for a predetermined period of time.

Referring to FIG. 3, in the step (d), during the heat treatment, a stirring apparent 27 is operatively connected to the lift arm 26 and is disposed in the inner casing 21' for stirring up the supplemental solution and the extracted liquid to form the combined solution.

Similarly, the step (1) further comprises the steps of:

(1-a) cutting the supplemental ingredients in pieces each having a size less than 5 cm;

(1-b) classifying the supplemental ingredients and putting the supplemental ingredients in a plurality of baskets, such as five baskets, respectively, wherein the baskets are piled up and the mesh holes of the baskets must be smaller than the size of the supplemental ingredients so that the boiling water is capable of passing through the mesh holes; and (1-c) Completely soaking the supplemental ingredients in water by fully immersing the baskets into the inner casing 21' of the extracting container 20.

The step (2) further comprises the steps of:

(2-a) heating the room temperature water inside the inner casing until the supplemental soaking solution is boiled and maintaining the supplemental soaking solution in boiling condition; and (2-b) inter-changing the piled-up positions of the baskets every predetermined time interval, preferably half an hour.

Similarly, by changing the positions of the baskets, the supplemental soaking solution at different levels can contact with different supplemental ingredients every predetermined time interval so as to soak the supplemental ingredients at different positions. Moreover, the taking out and placing back actions of the baskets can well mix and stir the supplemental soaking solution. The step (2-b)is repeated until the necessary chemicals from the supplemental ingredients are extracted into the supplemental soaking solution. According to the present invention, the step (2) takes about 2 hours to complete.

After the step (e), the producing method further comprises a step (f) of adding a predetermined amount of powered pearl into the combined liquid to form the Tien Hsien Liquid.

In the step (f), 65 mg of pearl powder, i.e. about 2–6% by weight, preferably a fine powder, is added into the combined solution in the inner casing 21' of the extracting container 20 in such a manner that the combined solution is further heated up and stirred to form the Tien Hsien liquid which can then be packed into bottles each having a predetermined capacity.

What is claimed is:

1. A method of producing a liquid composition, comprising the steps of:
   (a) putting a plurality of ingredients, which includes 11–20% by weight of ginseng, 30–50% by weight of cordyceps, and 11–20% by weight of ganoderma lucidum, in a plurality of baskets respectively, wherein said baskets are piled up and each has a plurality of mesh holes provided thereon;
   (b) completely soaking said ginseng, cordyceps and ganoderma lucidum in a predetermined weight of water within an extracting container to form a soaking solution by fully immersing said baskets into said extracting container, wherein said weight of said water is equal to a total weight of said ingredients and said water is capable of passing through said baskets through said mesh holes thereof;
   (c) heating said soaking solution to a temperature higher than a boiling point of said soaking solution while mixing and stirring said soaking solution every predetermined time interval until chemicals of said ingredients are extracted into said soaking solution; and
   (d) removing residuals of said ginseng, cordyceps and ganoderma lucidum from said soaking solution to form an extracted solution.

2. The method as recited in claim 1 wherein the step (c) further comprises the steps of:
   (c-1) heating said water inside said extracting container from room temperature to said boiling temperature of said soaking solution; and
   (c-2) inter-changing piled-up positions of said baskets every predetermined time interval, thereby by changing said piled-up positions of baskets, wherein said soaking solution at different levels is able to contact with different said ingredients every said predetermined time interval so as to soak said ingredients at different positions.

3. The method as recited in claim 2 wherein the step (c-2) includes the steps of taking said baskets out of said extracting container to change said piled-up positions of said baskets, and placing said baskets with new piled-up positions back inside said extracting container, wherein each of said taking out and placing back actions of said baskets substantially mixes and stirs said soaking solution.

4. The method as recited in claim 1 wherein, in the step (a), 10% or less by weight of honey is added to said ingredients soaked in said water to form said soaking solution.

5. The method as recited in claim 1 wherein, in the step (a), said ingredients are soaked in said water mixed with honey and sorbic acid to form said soaking solution.

6. The method as recited in claim 3 wherein, in the step (a), 10% of less by weight of honey is added to said ingredients soaked in said water to form said soaking solution.

7. The method as recited in claim 3 wherein, in the step (a), said ingredients are soaked in said water mixed with honey and sorbic acid to form said soaking solution.

8. The method as recited in claim 1 wherein, in the step (a), said ingredients include 425 mg of ginseng, 1150 mg of said cordyceps and 425 mg of said ganoderma lucidum which are soaked in 2000 of said water.

9. The method as recited in claim 6 wherein, in the step (a), said ingredients include 425 mg of said ginseng, 1150 mg of said cordyceps and 425 mg of said ganoderma lucidum which are soaked in 2000 mg of said water with said honey.

10. The method as recited in claim 7 wherein, in the step (a), said ingredients include 425 mg of said ginseng, 1150 mg of said cordyceps and 425 mg of said ganoderma lucidum which are soaked in 2000 mg of said water with said honey and said sorbic acid.

11. The method as recited in claim 10 wherein said step (c-1) said water inside said extracting container is heated for 30 to 45 minutes until said soaking solution is boiled, said piled-up positions of said baskets are inter-changed per every half an hour, and said steps (a) to (d) take 4 hours.

12. The method as recited in claim 1 further comprising the steps of:
   (e) mixing and stirring said extracted solution with a supplemental solution to form a combined solution; and
   (f) filtering said combined solution to obtain a combined liquid.

13. The method as recited in claim 3 further comprising the steps of:
   (e) mixing and stirring said extracted solution with a supplemental solution to form a combined solution; and
   (f) filtering said combined solution to obtain a combined liquid.

14. The method as recited in claim 5 further comprising the steps of:
   (e) mixing and stirring said extracted solution with a supplemental solution to form a combined solution; and
   (f) filtering said combined solution to obtain a combined liquid.

15. The method as recited in claim 7 further comprising the steps of:
   (e) mixing and stirring said extracted solution with a supplemental solution to form a combined solution; and
   (f) filtering said combined solution to obtain a combined liquid.

16. The method as recited in claim 10 further comprising the steps of:
   (e) mixing and stirring the extracted solution with a supplemental solution to form a combined solution; and
   (f) filtering said combined solution to obtain a combined liquid.

17. The method as recited in claim 12 wherein, in said step (e), supplemental ingredients of said supplemental solution include 8–22% by weight of Batatatis Rhizoma, 7–21% by weight of Astragalus, 4–12% by weight of Patchouli, 3–11% by weight of White Atractylodes, 3–11% by weight of Radiz Codonopsis, 3–11% by weight of Barbary Wolfberry, 2–6% by weight of Glossy Privet, and 2–6% by weight of Licorice.

18. The method as recited in claim 13 wherein, in said step (e), supplemental ingredients of said supplemental solution include 8–22% by weight of Batatatis Rhizoma, 7–21% by weight of Astragalus, 4–12% by weight of Patchouli, 3–11% by weight of White Atractylodes, 3–11% by weight of Radiz Codonopsis, 3–11% by weight of Barbary Wolfberry, 2–6% by weight of Glossy Privet, and 2–6% by weight of Licorice.

19. The method as recited in claim 15 wherein, in said step (e), supplemental ingredients of said supplemental solution include 8–22% by weight of Batatatis Rhizoma, 7–21% by weight of Astragalus, 4–12% by weight of Patchouli, 3–11% by weight of White Atractylodes, 3–11% by weight of Radiz Codonopsis, 3–11% by weight of Barbary Wolfberry, 2–6% by weight of Glossy Privet, and 2–6% by weight of Licorice.

20. The method as recited in claim 19 wherein said supplemental solution is produced by the steps of:
   (i) soaking said supplemental ingredients in a predetermined weight of water within said extracting container to form a supplemental soaking solution, wherein said weight of water is equal to a total weight of said supplemental ingredients;
   (ii) heating said supplemental soaking solution to a temperature higher than a boiling point of said supplemental soaking solution in said extracting container while mixing and stirring said supplemental soaking solution every predetermined time interval;
   (iii) removing residuals of said supplemental ingredients from said supplemental soaking solution to form said supplemental solution.

21. The method as recited in claim 18 wherein said supplemental solution is produced by the steps of:
   (i) soaking said supplemental ingredients in a predetermined weight of water within said extracting container to form a supplemental soaking solution, wherein said weight of water is equal to a total weight of said supplemental ingredients;
   (ii) heating said supplemental soaking solution to a temperature higher than a boiling point of said supplemental soaking solution in said extracting container while mixing and stirring said supplemental soaking solution every predetermined time interval;
   (iii) removing residuals of said supplemental ingredients from said supplemental soaking solution to form said supplemental solution.

22. The method as recited in claim 19 wherein said supplemental solution is produced by the steps of:
   (i) soaking said supplemental ingredients in a predetermined weight of water within said extracting container to form a supplemental soaking solution, wherein said weight of water is equal to a total weight of said supplemental ingredients;
   (ii) heating said supplemental soaking solution to a temperature higher than a boiling point of said supplemental soaking solution in said extracting container while mixing and stirring said supplemental soaking solution every predetermined time interval;
   (iii) removing residuals of said supplemental ingredients from said supplemental soaking solution to form said supplemental solution.

23. The method as recited in claim 16 wherein said supplemental solution is produced by the steps of:
   (i) soaking a plurality of supplemental ingredients, including 270 mg of Batatatis Rhizoma, 255 mg of Astragalus, 140 mg of Patchouli, 125 mg of White Atractylodes, 125 mg of Radiz Codonopsis, 125 mg of Barbary Wolfberry, 65 mg of Glossy Privet, and 65 mg of Licorice, in a predetermined weight of water within said extracting container;
   (ii) heating said supplemental soaking solution to a temperature higher than a boiling point of said supplemental soaking solution in said extracting container while mixing and stirring said supplemental soaking solution every predetermined time interval;
   (iii) removing residuals of said supplemental ingredients from said supplemental soaking solution to form a supplemental solution.

24. The method as recited in claim 20 wherein said step (i) further comprises the steps of:
   (i-a) putting said supplemental ingredients in a plurality of piled-up baskets with meshes holes thereon for enabling said water passing through; and
   (i-b) completely soaking said supplemental ingredients in water by fully immersing said baskets into said extracting container.

25. The method as recited in claim 22 wherein said step (i) further comprising the steps of:
   (i-a) putting said supplemental ingredients in a plurality of piled-up baskets with meshes holes thereon for enabling said water passing through; and
   (i-b) completely soaking said supplemental ingredients in water by fully immersing said baskets into said extracting container.

26. The method as recited in claim 23 wherein said step (i) further comprises the steps of:
   (i-a) putting said supplemental ingredients in a plurality of piled-up baskets with meshes holes thereon for enabling said water passing through; and
   (i-b) completely soaking said supplemental ingredients in water by fully immersing said baskets into said extracting container.

27. The method as recited in claim 24 wherein said step (ii) further comprises the steps of:
   (ii-a) heating said water inside said extracting container from room temperature to said boiling temperature of said supplemental soaking solution and maintaining said supplemental soaking solution in boiling condition; and
   (ii-b) inter-changing piled-up positions of said baskets every predetermined time interval.

28. The method as recited in claim 26 wherein said step (ii) further comprises said steps of:
   (ii-a) heating said water inside said extracting container from room temperature to said boiling temperature of said supplemental soaking solution and maintaining said supplemental soaking solution in boiling condition; and
   (ii-b) inter-changing piled-up positions of said baskets every predetermined time interval.

29. The method as recited in claim 12, after said step (f), further comprising a step (g) of adding and mixing a predetermined amount of powered pearl into said combined liquid.

30. The method as recited in claim 15, after said step (f), further comprising a step (g) of adding and mixing a predetermined amount of powered pearl into said combined liquid.

31. The method as recited in claim 16, after said step (f), further comprising a step (g) of adding and mixing a 65 mg of powered pearl into said combined liquid.

32. The method as recited in claim 20, after said step (f), further comprising a step (g) of adding and mixing a predetermined amount of powered pearl into said combined liquid.

33. The method as recited in claim 22, after said step (f), further comprising a step (g) of adding and mixing a predetermined amount of powered pearl into said combined liquid.

34. The method as recited in claim 23, after said step (f), further comprising a step (g) of adding a mixing a 65 mg of powered pearl into said combined liquid.

35. The method as recited in claim 27, after said step (f), further comprising a step (g) of adding and mixing a predetermined amount of powered pearl into said combined liquid.

36. The method as recited in claim 28, after said step (f), further comprising a step (g), of adding and mixing a predetermined amount of powered pearl into said combined liquid.

37. The method as recited in claim 29, after said step (f), further comprising a step (g) of adding and mixing a 65 mg of powered pearl into said combined liquid.

38. A liquid composition produced by a method which comprises the steps of:
   (a) soaking a plurality of ingredients, which includes 11–20% by weight of ginseng, 30–50% by weight of cordyceps, and 11–20% by weight of ganoderma lucidum, in a predetermined weight of water within an extracting container to form a soaking solution, wherein said weight of water is equal to a total weight of said ingredients;
   (b) heating said soaking solution to a temperature higher than a boiling point of said soaking solution while mixing and stirring said soaking solution every predetermined time interval; and
   (c) removing said residuals of said ginseng, cordyceps and ganoderma lucidum from said soaking solution.

39. The liquid composition as recited in claim 38 wherein the step (a) comprises the steps of:
   (a-1) putting said ginseng, cordyceps and ganoderma lucidum in a plurality of baskets respectively, wherein said baskets are piled up and each has a plurality of mesh holes provided thereon for said water to pass through said baskets; and
   (a-2) completely soaking said ginseng, cordyceps and ganoderma lucidum in said water by fully immersing said baskets into said extracting container.

40. The liquid composition as recited in claim 39 wherein the step (b) further comprises the steps of:
   (b-1) heating said water inside said extracting container from room temperature to said boiling temperature of said soaking solution; and
   (b-2) inter-changing piled-up positions of said baskets every predetermined time interval, thereby by changing said piled-up positions of baskets, wherein said soaking solution at different levels is able to contact with different said ingredients every said predetermined time interval so as to soak said ingredients at different positions.

41. The liquid composition as recited in claim 40 wherein the step (b-2) includes the steps of taking said baskets out of said extracting container vertically to change said piled-up positions of said baskets, and placing said baskets with new piled-up positions back inside said extracting contain, wherein each of said taking out and placing back actions of said baskets substantially mixes and stirs said soaking solution.

42. The liquid composition as recited in claim 41 wherein, in the step (a), said ingredients are soaked in said water mixed with honey and sorbic acid to form said soaking solution.

43. The liquid composition as recited in claim 42 wherein, in the step (a), said ingredients include 425 mg of said ginseng, 1150 mg of said cordyceps and 425 mg of said ganoderma lucidum which are soaked in 2000 mg of said water with said honey and said sorbic acid.

44. The liquid composition as recited in claim 43 wherein said step (b-1) said water inside said extracting container is heated for 30 to 45 minutes until said soaking solution is boiled, said piled-up positions of said baskets are inter-changed per every half an hour, and said steps (a) to (c) take 4 hours.

45. The liquid composition as recited in claim 41 wherein said method further comprises the steps of:
   (d) mixing and stirring said extracted solution with a supplemental solution to form a combined solution; and
   (e) filtering said combined solution to obtain a combined liquid.

46. The liquid composition as recited in claim 42 wherein said method further comprises the steps of:
   (d) mixing and stirring said extracted solution with a supplemental solution to form a combined solution; and
   (e) filtering said combined solution to obtain a combined liquid.

47. The liquid composition as recited in claim 43 wherein said method further comprises the steps of:
   (d) mixing and stirring said extracted solution with a supplemental solution to form a combined solution; and
   (e) filtering said combined solution to obtain a combined liquid.

48. The liquid composition as recited in claim 45 wherein, in said step (d), supplemental ingredients of said supplemental solution include 8–22% by weight of Batatatis Rhizoma, 7–21% by weight of Astragalus, 4–12% by weight of Patchouli, 3–11% by weight of White Atractylodes, 3–11% by weight of Radiz Codonopsis, 3–11% by weight of Barbary Wolfberry, 2–6% by weight of Glossy Privet, and 2–6% by weight of Licorice.

49. The liquid composition as recited in claim 46 wherein, in said step (d), supplemental ingredients of said supplemental solution include 8–22% by weight of Batatatis Rhizoma, 7–21% by weight of Astragalus, 4–12% by weight of Patchouli, 3–11% by weight of White Atractylodes, 3–11% by weight of Radiz Codonopsis, 3–11% by weight of Barbary Wolfberry, 2–6% by weight of Glossy Privet, and 2–6% by weight of Licorice.

50. The liquid composition as recited in claim 48 wherein said supplemental solution is produced by the steps of:
   (i) soaking said supplemental ingredients in a predetermined weight of water within said extracting container to form a supplemental soaking solution, wherein said weight of water is equal to a total weight of said supplemental ingredients;
   (ii) heating said supplemental soaking solution to a temperature higher than a boiling point of said supplemental soaking solution in said extracting container while mixing and stirring said supplemental soaking solution every predetermined time interval;
   (iii) removing residuals of said supplemental ingredients from said supplemental soaking solution to form said supplemental solution.

51. The liquid composition as recited in claim 49 wherein said supplemental solution is produced by the steps of:
   (i) soaking said supplemental ingredients in a predetermined weight of water within said extracting container to form a supplemental soaking solution, wherein said weight of water is equal to a total weight of said supplemental ingredients;

(ii) heating said supplemental soaking solution to a temperature higher than a boiling point of said supplemental soaking solution in said extracting container while mixing and stirring said supplemental soaking solution every predetermined time interval;

(iii) removing residuals of said supplemental ingredients from said supplemental soaking solution to form said supplemental solution.

52. The liquid composition as recited in claim 47 wherein said supplemental solution is produced by the steps of:

(i) soaking a plurality of supplemental ingredients, including 270 mg of Batatatis Rhizoma, 255 mg of Astragalus, 140 mg of Patchouli, 125 mg of White Atractylodes, 125 mg of Radiz Codonopsis, 125 mg of Barbary Wolfberry, 65 mg of Glossy Privet, and 65 mg of Licorice, in a predetermined weight of water within said extracting container;

(ii) heating said supplemental soaking solution to a temperature higher than a boiling point of said supplemental soaking solution in said extracting container while mixing and stirring said supplemental soaking solution every predetermined time interval;

(iii) removing residuals of said supplemental ingredients from said supplemental soaking solution to form a supplemental solution.

53. The liquid composition as recited in claim 50 wherein said step (i) further comprises the steps of:

(i-a) putting said supplemental ingredients in a plurality of piled-up baskets with meshes holes thereon for enabling said water passing through; and (i-b) completely soaking said supplemental ingredients in water by fully immersing said baskets into said extracting container.

54. The liquid composition as recited in claim 51 wherein said step (i) further comprises the steps of:

(i-a) putting said supplemental ingredients in a plurality of piled-up baskets with meshes holes thereon for enabling said water passing through; and (i-b) completely soaking said supplemental ingredients in water by fully immersing said baskets into said extracting container.

55. The liquid composition as recited in claim 52 wherein said step (i) further comprises the steps of:

(i-a) putting said supplemental ingredients in a plurality of piled-up baskets with meshes holes thereon for enabling said water passing through; and (i-b) completely soaking said supplemental ingredients in water by fully immersing said baskets into said extracting container.

56. The liquid composition as recited in claim 53 wherein said step (ii) further comprises said steps of:

(ii-a) heating said water inside said extracting container from room temperature to said boiling temperature of said supplemental soaking solution and maintaining said supplemental soaking solution in boiling condition; and (ii-b) inter-changing piled-up positions of said baskets every predetermined time interval.

57. The liquid composition as recited in claim 54 wherein said step (ii) further comprises said steps of:

(ii-a) heating said water inside said extracting container from room temperature to said boiling temperature of said supplemental soaking solution and maintaining said supplemental soaking solution in boiling condition; and (ii-b) inter-changing piled-up positions of said baskets every predetermined time interval.

58. The liquid composition as recited in claim 55 wherein said step (ii) further comprises said steps of:

(ii-a) heating said water inside said extracting container from room temperature to said boiling temperature of said supplemental soaking solution and maintaining said supplemental soaking solution in boiling condition; and (ii-b) inter-changing piled-up positions of said baskets every predetermined time interval.

59. The liquid composition as recited in claim 56, after said step (e), further comprising a step (f) of adding and mixing a predetermined amount of powered pearl into said combined liquid.

60. The liquid composition as recited in claim 57, after said step (e), further comprising a step (f) of adding and mixing a predetermined amount of powered pearl into said combined liquid.

61. The liquid composition as recited in claim 58, after said step (e), further comprising a step (f) of adding and mixing a 65 mg of powered pearl into said combined liquid.

* * * * *